United States Patent
Imanaka et al.

(10) Patent No.: US 6,669,932 B2
(45) Date of Patent: Dec. 30, 2003

(54) SKIN-WHITENING COSMETIC

(75) Inventors: Hiromichi Imanaka, Osaka (JP); Hideya Ando, Osaka (JP); Taketoshi Makino, Osaka (JP)

(73) Assignee: Sunstar Inc., Osaka (JP)

( * ) Notice: Subject to any disclaimer, the term of this patent is extended or adjusted under 35 U.S.C. 154(b) by 0 days.

(21) Appl. No.: 09/445,562

(22) PCT Filed: Jun. 9, 1998

(86) PCT No.: PCT/JP98/02548
§ 371 (c)(1),
(2), (4) Date: Mar. 14, 2000

(87) PCT Pub. No.: WO98/56338
PCT Pub. Date: Dec. 17, 1998

(65) Prior Publication Data
US 2003/0103916 A1 Jun. 5, 2003

(30) Foreign Application Priority Data
Jun. 10, 1997 (JP) ............................................. 9-169590

(51) Int. Cl.[7] ............................ A61K 9/127; A61K 7/48
(52) U.S. Cl. ........................... 424/62; 424/401; 424/450
(58) Field of Search ................................ 424/401, 450, 424/62; 514/54

(56) References Cited

U.S. PATENT DOCUMENTS

| | | | | |
|---|---|---|---|---|
| 4,938,960 A | | 7/1990 | Ismail | |
| 5,279,834 A | * | 1/1994 | Meybeck | |
| 5,560,907 A | * | 10/1996 | Sakai | 424/62 |
| 5,932,608 A | * | 8/1999 | Nguyen | 514/415 |
| 5,980,904 A | * | 11/1999 | Leverett | 424/195.1 |
| 6,174,533 B1 | * | 1/2001 | SaNogueira | 424/401 |

FOREIGN PATENT DOCUMENTS

| | | | |
|---|---|---|---|
| GB | 2150433 A | 7/1985 | |
| GB | 2283173 A | 5/1995 | |
| JP | 02096509 | * 4/1990 | |
| JP | 2-207013 | 8/1990 | ............ A61K/7/00 |
| JP | 5-39485 | 2/1993 | ........... C09K/19/50 |
| JP | 7-509001 | 10/1995 | .......... A61K/31/20 |
| JP | 06040886 | * 2/1996 | |
| JP | 1186811 | 1/1998 | |
| JP | 63-239208 | 10/1998 | ............ A61K/7/00 |

* cited by examiner

Primary Examiner—Gollamudi S. Kishore
(74) Attorney, Agent, or Firm—Sughrue Mion, PLLC (57) ABSTRACT

A skin-whitening cosmetic material which contains an unsaturated fatty acid or a derivative thereof as the active ingredient, is highly effective in making the color of pigmentation on the skin lighter at a lower concentration, and is highly safe. The skin-whitening cosmetic material comprises (A) at least one member selected from unsaturated fatty acids having from 18 to 22 carbon atoms and having from 2 to 6 double bonds in the molecular structure, and derivatives thereof, (B) a phospholipid, (C) an antioxidant, (D) at least one member selected from proteins and hydrolyzates thereof, and (E) at least one member selected from muco-polysaccharides and salts thereof.

10 Claims, 2 Drawing Sheets

SKIN-WHITENING COSMETIC

This application is a 371 of PCT/JP98/02548 filed Jun. 9, 1998.

TECHNICAL FIELD

The present invention relates to a skin-whitening cosmetic material with which skin blackening or skin pigmentation such as spots and freckles due to UV rays is removed, reduced (whitened) or prevented.

BACKGROUND ART

Dyspigmentation is one symptom of skin aging, which gives spots such as chloasmata (liver spots) and senile spots. It is known that dyspigmentation is exacerbated by ultra-violet rays. To prevent dyspigmentation, used are UV protectors. To relieve dyspigmentation which has already produced spots, used are skin-whitening cosmetic materials comprising, as the active ingredient, any of vitamin C, placenta extract, kojic acid, arbutin, unsaturated fatty acids, etc. Of those, it is known that unsaturated fatty acids such as typically linoleic acid or linolic acid have an excellent effect of reducing or whitening pigmentation caused on the skin (see the *Journal of the Cosmetician Association of Japan*, Vol. 27, pp. 415–423, 1993).

However, skin-whitening cosmetic materials comprising unsaturated fatty acids such as linoleic acid or linolic acid are problematic in that the endermic absorption of unsaturated fatty acids having been applied to the skin is often prevented by the barrier function of the skin with the result that the skin-whitening cosmetic materials applied to the skin could not exhibit so much the effect of reducing or whitening pigmentation to the degree as expected. Therefore, in order to make them exhibit a high skin-whitening effect, skin-whitening cosmetic materials must contain a large amount of unsaturated fatty acids, but cause unfavorable skin troubles.

Some reports are known, which disclose emulsified cosmetics (see Japanese Patent Application Laid-Open (JP-A) Hei-5-70332) or liniments for external use (JP-A Hei-5-70334) comprising unsaturated fatty acids, phospholipids, and proteins or their decomposates; and skin-treating and protecting agents comprising unsaturated fatty acids, phospholipids and vitamin E (see JP-A Sho-61-40210). However, the skin-whitening effect of those known materials is poor.

On the other hand, it is well known that liposomes are effective as carriers. For example, known are liposomes comprising linoleic acid or linolic acid as the active ingredient, which are said effective for acne, blackheads, pimples, pustules, etc. (see Published Japanese translation of PCT international publication for patent application (JP-W) Hei-7-509001). However, the stability of the cosmetic materials comprising such liposomes is not satisfactory, and the effective amount of linoleic acid or linolic acid to be in those liposomes is at least 1% by weight or more. Thus, it is hard to say that know liposome exhibit a sufficient effect at a low concentration of the active ingredient.

Accordingly, an object of the present invention is to provide a skin-whitening cosmetic material which comprises, as the active ingredient, an unsaturated fatty acid or a derivative thereof, which is highly effective for reducing or whitening pigmentation caused on the skin even in a lower concentration of the active ingredient and is highly safe.

DISCLOSURE OF THE INVENTION

We, the present inventors have assiduously studied in order to attain the object noted above, and, as a result, have found surprisingly that a skin-whitening cosmetic material comprising phospholipids, antioxidants, proteins or their decomposates, muco-polysaccharides or their salts, along with unsaturated fatty acids such as linoleic acid or linolic acid exhibits an excellent effect for reducing or whitening skin spots even though it contains a reduced amount of unsaturated fatty acids, and that the safety of the material is high. On the basis of these findings, we have completed the present invention.

Specifically, the invention provides a skin-whitening cosmetic material comprising;

(A) at least one member selected from unsaturated fatty acids having from 18 to 22 carbon atoms and having from 2 to 6 double bonds in the molecular structure, and their derivatives, (B) a phospholipid, (C) an antioxidant, (D) at least one member selected from proteins and their hydrolyzates, and (E) at least one member selected from muco-polysaccharides and their salts.

Preferably, the skin-whitening cosmetic material of the invention comprises liposomal composites of those ingredients (A) to (E).

The invention also provides a skin-whitening cosmetic material comprising liposomal composites of the ingredients (A) to (E).

BEST MODE FOR CARRYING OUT THE INVENTION

Now, the invention is described in detail herein under.

The unsaturated fatty acids and their derivatives to be used as the component (A) in the cosmetic material of the invention have from 18 to 22 carbon atoms in the fatty acid moiety and from 2 to 6 double bonds in the molecular structure. The fatty acids of that type include, for example, free unsaturated fatty acids, such as linoleic acid or linolic acid, α-linolenic acid, γ-linolenic acid, dihomo-γ-linolenic acid, arachidonic acid, eicosapentaenoic acid, docosahexaenoic acid, etc.; metal salts of unsaturated fatty acids, such as sodium linoleate, potassium α-linolenate, etc.; amino acid salts of unsaturated fatty acids, such as arginine linoleate, lysine α-linolenate, etc.; amine salts of unsaturated fatty acids, such as triethanolamine linoleate, monoethanolamine α-linolenate, etc.; and mono-esters and di-esters of unsaturated fatty acids, such as ethyl linoleate, ethyl a-linolenate, linoleic acid monoglyceride, α-linolenic acid monoglyceride, linoleic acid diglyceride, α-linolenic acid diglyceride, etc. Triglycerides of unsaturated fatty acids existing in ordinary vegetable oils and fats are excluded. Of those fatty acids, preferred are linoleic acid or linolic acid, α-linolenic acid, ethyl linoleate, ethyl α-linolenate, linoleic acid monoglyceride, and α-linolenic acid monoglyceride, and especially preferred is linoleic acid. One or more of those unsaturated fatty acids and their derivatives may be in the composition.

The amount of the unsaturated fatty acids and their derivatives to be in the cosmetic material of the invention may be from 0.01 to 0.7% by weight, preferably from 0.03 to 0.5% by weight, and most preferably from 0.05 to 0.3% by weight. If the amount is smaller than the defined range, the effect of the cosmetic material to reduce or whiten pigmentation may be unsatisfactory. However, even if the amount is larger than the defined range, the effect of the cosmetic material tends to be no more augmented.

The phospholipids of the component (B) include, for example, natural lecithins, such as phosphatidyl choline, phosphatidyl serine, phosphatidyl ethanolamine, phosphatidyl inositol, phosphatidyl glycerol, sphingomyelin, soybean lecithin, corn lecithin, cotton seed oil lecithin, egg yolk lecithin, egg white lecithin, etc.; hydrogenated lecithins; and phospholipid derivatives as formed by introducing polyethylene glycol or aminoglycans into those phospholipids. One or more of those phospholipids may be in the composition. Of those phospholipids, preferred are soybean lecithin, egg yolk lecithin, hydrogenated soybean lecithin, and hydrogenated egg yolk lecithin.

The amount of the phospholipids in the cosmetic material may be from 0.05 to 10% by weight, and preferably from 0.20 to 2% by weight. If the amount is smaller than the defined range, the effect in reducing or whitening pigmentation may not be found. Even if the amount is larger than the defined range, the effect of the cosmetic material tends to be no more augmented.

The antioxidants of the component (C) include, for example, dibutylhydroxytoluene, butylhydroxyanisole, vitamin E and its derivatives, vitamin C and its derivatives, erythorbic acid and its salts, vegetable extracts such as cranesbill extract, hamamelis extract, tea extract, etc., and gallates. Of those, preferred are vitamin E, dibutylhydroxytoluene, butyl-hydroxyanisole, and gallates, and especially preferred is vitamin E. One or more of those antioxidants may be in the composition. The amount of the antioxidants in the cosmetic material may be from 0.005 to 0.5% by weight, and preferably from 0.01 to 0.2% by weight. If the amount is smaller than the defined range, the effect of the cosmetic material to reduce or whiten pigmentation may not last long. On the other hand, if the amount is larger than the defined range, the stability of the cosmetic material may be lowered.

The proteins and their hydrolyzates of the component (D) for use in the invention include, for example, collagen, elastin, keratin, casein, and their hydrolyzates, salts of such hydrolyzates, esters of such hydrolyzates, and enzyme-processed proteins and protein hydrolyzates. Of those, preferred are collagen, elastin and their hydrolyzates, salts of such hydrolyzates, and esters of such hydrolyzates, which include, for example, hydrolyzed collagen, atelocollagen, hydrolyzed sodium casein, hydrolyzed ethyl collagen, and water-soluble collagen. One or more of those proteins and their hydrolyzates may be in the composition. The amount of the component (D) maybe from 0.001 to 0.5% by weight, and preferably from 0.01 to 0.1% by weight. If the amount is smaller than the defined range, the effect in reducing or whitening pigmentation may not be found. If the amount is larger than the defined range, the effect of the cosmetic material tends to be no more augmented.

The muco-polysaccharides of the component (E) include, for example, chondroitin sulfate, hyaluronic acid, dermatan sulfate, heparan sulfate, mucoitin sulfate, heparin and its derivatives, and their sodium salts and potassium salts. Of those, preferred are chondroitin sulfate, hyaluronic acid and their sodium salts. The muco-polysaccharides may be derived from natural substances or may be produced in biochemical methods. One or more of those muco-polysaccharides may be in the composition.

The amount of the muco-polysaccharides may be from 0.0005 to 0.5% by weight, and preferably from 0.001 to 0.1% by weight. If the amount is smaller than the defined range, the cosmetic material may be ineffective in reducing or whitening pigmentation. If the amount is larger than the defined range, the feel of the cosmetic material may be worsened.

Production of Cosmetic Material:

To produce the skin-whitening cosmetic material of the invention, the ingredients (A) to (E) noted above may be mixed and formulated in any ordinary manner, according to the intended form of the cosmetic material, to give ordinary formulations of milky lotion, cream, lotion, essence, cleansing, pack, face wash, etc.

Alternatively, a liposomal composite containing the components (A) to (E) is previously prepared, and it may be formulated to give desired formulations. Using the liposomal composite is preferred, since it produces a high skin-whitening effect even though the concentration of the active ingredients therein is low and since the stability of the active ingredients therein is increased so that the cosmetic material comprising it is hardly deteriorated.

(a) In the invention, a first method of producing the liposomal composite comprises forming liposomes that contain the component (A) of unsaturated fatty acids and their derivatives, the component (B) of phospholipids and the component (C) of antioxidants of the indispensable ingredients, followed by dispersing and mixing the resulting liposomes in a mixture comprising the component (D) of proteins and their hydrolyzates and the component (E) of muco-polysaccharides. This method is hereinafter referred to as Method A.

(b) A second method of producing the liposomal composite comprises forming liposomes that contain the component (A) of unsaturated fatty acids and their derivatives, the component (B) of phospholipids and the component (C) of antioxidants, in a mixture comprising the component (D) of proteins and their hydrolyzates and the component (E) of muco-polysaccharides. This method is hereinafter referred to as Method B.

In one preferred embodiment of the invention, a liposomal composite containing the indispensable ingredients noted above is first prepared and then formulated into desired formulations of a skin-whitening cosmetic material. Especially preferred is mixing and dispersing the liposomal composite in cosmetic media. For this, preferred are water-soluble cosmetic media. Examples of this embodiment include cosmetic lotions, gels, essences and oil-in-water emulsions.

Preparation of Liposomal Composite:

Now, preferred methods for producing liposomal composites to be in the cosmetic material of the invention are illustrated hereinunder, which, however, are not limitative.

Method A

Liposomes containing the component (A) of unsaturated fatty acids and their derivatives, the component (B) of phospholipids and the component (C) of antioxidants are prepared according to any of the methods (1) to (4) mentioned below.

(1) A phospholipid, an unsaturated fatty acid or its salt or ester, and an antioxidant are homogenized, and then hydrated with an aqueous solution containing a pH-adjusting agent, a polyhydric alcohol, a saccharide and the like, to give liposomes containing the unsaturated fatty acid or its salt or ester.

(2) A phospholipid, an unsaturated fatty acid or its salt or ester, and an antioxidant are dissolved in an alcohol or polyhydric alcohol, and then hydrated with an aqueous solution containing a pH-adjusting agent, a polyhydric alcohol, a saccharide and the like, to give liposomes.

(3) Using an ultrasonic wave generator or a French press, a phospholipid, an unsaturated fatty acid or its salt or ester, and an antioxidant are complexed in water to give liposomes.

(4) A phospholipid, an unsaturated fatty acid or its salt or ester, and an antioxidant are mixed and dissolved in ethanol, then the resulting ethanolic solution is added to an aqueous solution of potassium chloride, and thereafter ethanol is removed from the resulting mixture to give liposomes.

The liposomal dispersion thus prepared is, if desired, passed through a filter to dress the liposomes. Also if desired, any of polymer substances such as carboxyvinyl polymer, carboxymethyl cellulose, hydroxyethyl cellulose, xanthane gum, poly(oxyethylene)-poly(oxypropylene) block copolymer, etc.; pH-adjusting agents such as citric acid, salts of citric acid, phosphoric acid, salts of phosphoric acid, triethanolamine, potassium hydroxide, sodium hydroxide, lactic acid, salts of lactic acid, etc.; polyhydric alcohols such as glycerin, propylene glycol, butylene glycol, etc.; polysaccharides such as salts of alginic acid, esters of alginic acid, etc.; saccharides such as trehalose, glucose, sorbitol, sucrose, etc.; and cholesterol may be added to the liposomal dispersion in order to improve the stability of the dispersion.

The ratio of the unsaturated fatty acid or its salt or ester to the phospholipid to form liposomes is preferably from 1/5 to 2/1 by mol, more preferably from 1/2 to 3/2 by mol, as the liposomes comprising them in the ratio falling within the defined range produce a higher skin-whitening effect.

Preparation of Liposomal Composite:

Next, the liposomal dispersion as prepared according to any of the methods noted above is dispersed in an aqueous solution comprising a protein or its decomposate and a muco-polysaccharide. Thus is obtained a liposomal composite containing a phospholipid, an unsaturated fatty acid or its salt or ester, an antioxidant, a protein and a muco-polysaccharide.

Method B

A second method of producing the liposomal composite for use in the invention comprises forming liposomes that contains the components (A), (B) and (C) in a mixture containing the components (D) and (E), for example, as in the following methods (1) to (3).

(1) A phospholipid, an unsaturated fatty acid or its salt or ester, and an antioxidant are homogenized, and the resulting homogenate is dispersed in an aqueous solution containing a protein or its decomposate and a muco-polysaccharide to form a liposomal composite. In this method, if desired, a pH-adjusting agent, a polyhydric alcohol, a saccharide and the like may be added to the aqueous solution.

(2) A phospholipid, an unsaturated fatty acid or its salt or ester, and an antioxidant are dissolved in an alcohol, a polyhydric alcohol or the like, and the resulting solution is hydrated with an aqueous solution containing a protein or its decomposate and a muco-polysaccharide to form a liposomal composite. In the step of hydration, a pH-adjusting agent or the like may be added to the system.

(3) Using an ultrasonic wave generator or a French press, a phospholipid, an unsaturated fatty acid or its salt or ester, and an antioxidant are complexed in an aqueous solution containing a protein or its decomposate and a muco-polysaccharide to form a liposomal composite. In this method, if desired, a pH-adjusting agent, a polyhydric alcohol, a saccharide and the like may be added to the aqueous solution.

The liposomal composite dispersion thus prepared according to any of the methods (B) (1) to (3) is, if desired, passed through a filter to dress the liposomes. Also, if desired, any of polymer substances such as carboxyvinyl polymer, carboxymethyl cellulose, hydroxyethyl cellulose, xanthane gum, poly(oxyethylene)-poly(oxypropylene) block copolymer, etc.; pH-adjusting agents such as citric acid, salts of citric acid, phosphoric acid, salts of phosphoric acid, triethanolamine, potassium hydroxide, sodium hydroxide, lactic acid, salts of lactic acid, etc.; polyhydric alcohols such as glycerin, propylene glycol, butylene glycol, etc.; polysaccharides such as salts of alginic acid, esters of alginic acid, etc.; saccharides such as trehalose, glucose, sorbitol, sucrose, etc.; and cholesterol may be added to the liposomal dispersion in order to improve the stability of the dispersion. The ratio of the unsaturated fatty acid or its salt or ester to the phospholipid to form liposomes is preferably from 1/5 to 2/1 by mol, more preferably from 1/2 to 3/2 by mol, as the liposomes comprising them in the ratio falling within the defined range produce a higher skin-whitening effect.

The skin-whitening cosmetic material of the invention thus produced in the manner mentioned hereinabove is more effective in reducing or whitening pigmentation caused on the skin than any other conventional skin-whitening cosmetic materials, even though the concentration of the unsaturated fatty acid in the cosmetic material of the invention is much lower than that in the conventional cosmetic materials. In addition, the cosmetic material of the invention is highly safe.

Other Additives:

The skin-whitening cosmetic material of the invention may optionally contain any of anti-inflammatory agents, UV absorbents, UV reflectors, skin whiteners except the essential component (A), oils, surfactants, moisturizers, animal and vegetable extracts, pH-adjusting agents, colorants, fragrances, preservatives, and chelating agents, within the range not interfering with the effect of the material.

The anti-inflammatory agents include, for example, allantoin, epsilon-aminocaproic acid, glycyrrhetinic acid, glycyrrhizic acid, their salts and derivatives, photosensitive substance No. 301, photosensitive substance No. 401, diphenhydramine hydrochloride, water-soluble azulenes (salts of 1,4-dimethyl-7-isopropylazulene-2-sulfonic acid), adenosine monophosphate, lithospermun root extract, ligusticum root extract, mugwort extract, burnet extract, etc. One or more of these may be added to the composition. The amount of the anti-inflammatory agent to be in the composition is preferably from 0.01 to 5% by weight.

The UV absorbents include, for example, urocanic acid, ethyl urocanate, oxybenzone, oxybenzone-sulfonic acid, tetrahydroxybenzophenone, sodium dihydroxydimethoxybenzo-phenone-sulfonate, dihydroxydimethoxybenzophenone, dihydroxybenzophenone, cinoxate, methyl diisopropylcinnamate, octyl methoxycinnamate, glyceryl para-aminobenzoate, amyl para-dimethylaminobenzoate, octyl para-dimethylaminobenzoate, para-aminobenzoic acid, ethyl para-aminobenzoate, butyl-methoxybenzoylmethane, etc. The UV reflectors include, for example, titanium oxide grains, zinc oxide grains, iron oxide grains, silicone-coated grains of those UV reflectors. One or more of those UV absorbents and reflectors may be added to the composition. The amount of the UV absorbent or reflector to be in the composition may be from 0.05 to 25% by weight.

The composition of the invention may contain any other skin whiteners except the essential component (A). For example, it may contain one or more of ascorbic acid and its salts and esters, placenta extract, kojic acid and its salts and esters, glucosamine and its salts and esters, azelaic acid and its salts and esters, retinol and its salts and esters, pyridoxine and its salts and esters, tranexamic acid and its salts and esters, arbutin, photosensitive substances, sulfur, 4-hydroxycinnamic acid, ginseng extract, licorice root extract, etc. The amount of the additional skin whitener to be in the composition may be from 0.1 to 10.0% by weight.

EXAMPLES

Now, the invention is described in more detail by means of the following Examples and Comparative Examples, which, needless-to-say, are not intended to restrict the scope of the invention. Unless otherwise specifically indicated, "%" in Examples and Comparative Examples is by weight.

Examples 1 to 9, and Comparative Examples 1 to 17

The ingredients shown in Tables 1 and 2 along with their amounts were formulated into skin-whitening cosmetic materials, which were then evaluated. The methods of formulating them and the methods of evaluating them are mentioned below.

[Formulation of Cosmetic Materials]

The ingredients shown in Tables 1 and 2 were formulated according to the methods mentioned below to prepare cosmetic materials of Examples 1 to 9 and Comparative Examples 1 to 17, which were then evaluated.

[Formulation of Cosmetic Materials of Examples 1, 2 and 6, and Comparative Examples 1 to 17]

Collagen and sodium chondroitin sulfate were dissolved in purified water, to which was added a mixture of lecithin or hydrogenated lecithin, the unsaturated fatty acid indicated, and vitamin E, along with 1,3-butylene glycol, carboxyvinyl polymer, potassium hydroxide, and methyl para-hydroxybenzoate, and mixed by stirring them. Thus were prepared essence samples. [Formulation of Cosmetic Materials of Examples 3, 5 and 9, in which was prepared a liposomal composite by Method B]

Lecithin or hydrogenated lecithin, the unsaturated fatty acid indicated, and vitamin E were mixed with 1,3-butylene glycol and homogenized. Next, the resulting homogenate was added to a solution of collagen and sodium chondroitin sulfate in purified water, and mixed by stirring them. Then, this was processed in a French press to form a liposomal composite. The resulting liposomal composite was added to a solution of 1,3-butylene glycol, carboxyvinyl polymer, potassium hydroxide and methyl para-hydroxybenzoate in purified water, and mixed by stirring them. Thus were prepared essence samples. Formulation of Cosmetic Materials of Examples 4, 7 and 8, in which was prepared a liposomal composite by Method A:

Lecithin or hydrogenated lecithin, the unsaturated fatty acid indicated, and vitamin E were dissolved in a solvent such as methylene chloride, and homogenized. Then, purified water was added to the resulting homogenate, from which the solvent had been removed, and mixed by stirring them. The resulting mixture was processed in a French press to form liposomes. The liposomes were added to a solution of collagen and sodium chondroitin sulfate in purified water. The resulting mixture was added to a solution of 1,3-butylene glycol, carboxyvinyl polymer, potassium hydroxide and methyl para-hydroxybenzoate in purified water, and mixed by stirring them. Thus were prepared essence samples.

[Evaluation of Cosmetic Materials]

1. Test for reducing or whitening pigmentation (anti-pigmentation):

Herein used were brown English guinea pigs as test animals. The back of each test animal was shaven, and exposed to UV rays (UVB strength: 1 $J/cm^2$) twice a week for 2 weeks. After having been left for 1 week, all test animals had a stable pigmentation portion. Each sample obtained in the Examples and Comparative Examples was applied to the pigmentation portion of each test animal, once a day for continuous 4 weeks. During this application test, the degree of pigmentation being treated with each sample was visually observed on the first day of each week, and the effect of each sample to reduce or whiten pigmentation was evaluated according to the criteria mentioned below. Of some test animals, the lightness (L) of the pigmentation portions being treated with the sample was measured using a calorimeter.

(Criteria for the degree of pigmentation)

−: The sample had no effect in reducing or whitening pigmentation.

±: The sample had a little effect in reducing or whitening pigmentation.

+: The sample had an effect in reducing or whitening pigmentation in a middle degree.

++: The sample had effect in reducing or whitening pigmentation in a high degree.

2. Test for skin penetrability:

The samples of Example 4, and Comparative Examples 4 and 11 were tested for the skin penetrability of linoleic acid or linolic acid in those samples. Hairless mice were used as test animals herein. The back skin of each test animal was peeled, and stretched in a diffusion cell containing a physiological saline solution as the reservoir. While the skin was incubated in the cell at 37° C., 0.5 ml of each sample was applied onto the skin. Linoleic acid or linolic acid was extracted from the skin as sampled at predetermined time intervals. Then, linoleic acid or linolic acid finally remained in the skin was recovered. The both were quantified through high-performance liquid chromatography. Based on the amount (100) of linoleic acid or linolic acid having finally remained in the skin, the degree of time-dependent penetration of linoleic acid or linolic acid into the skin at the sampling time was calculated.

Figure 1:
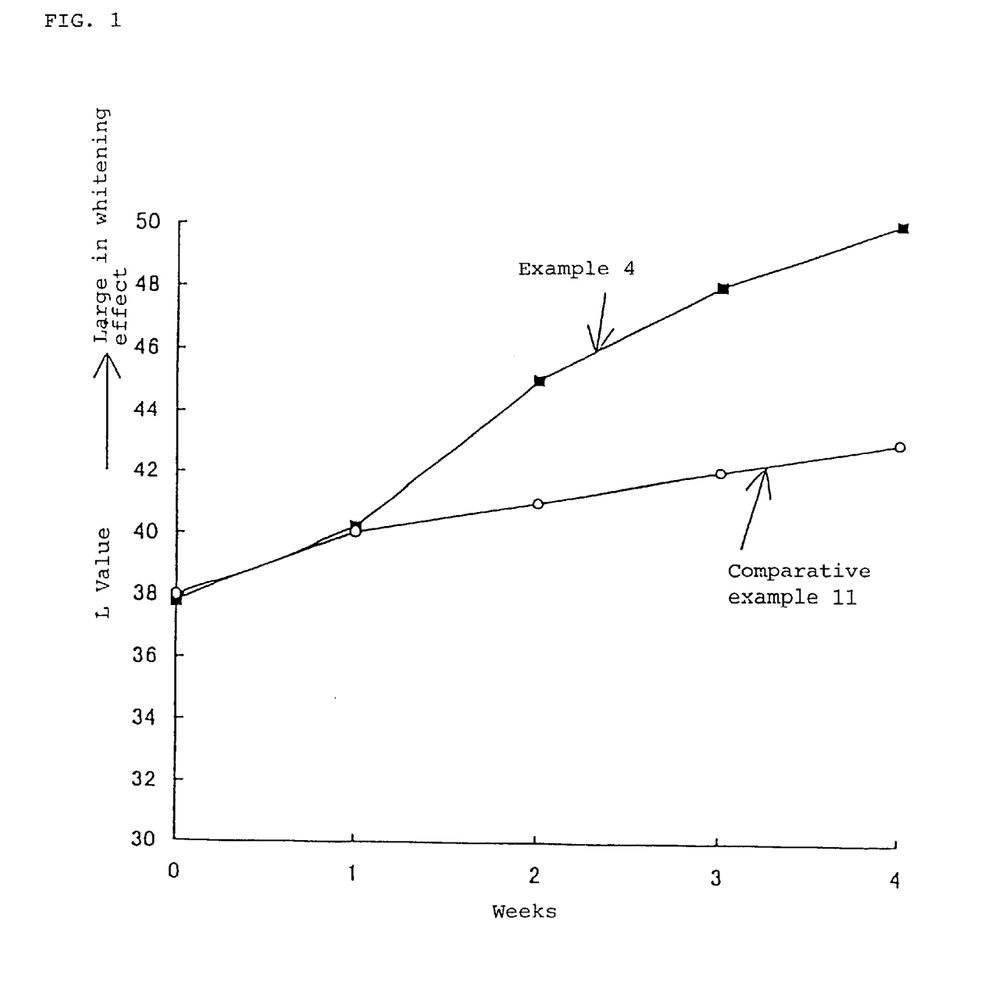
FIG. 1 is a graph showing the relationship between the period of time after application of samples of a skin-whitening cosmetic material to the skin, and the skin-whitening effect of the samples.
Figure 2:
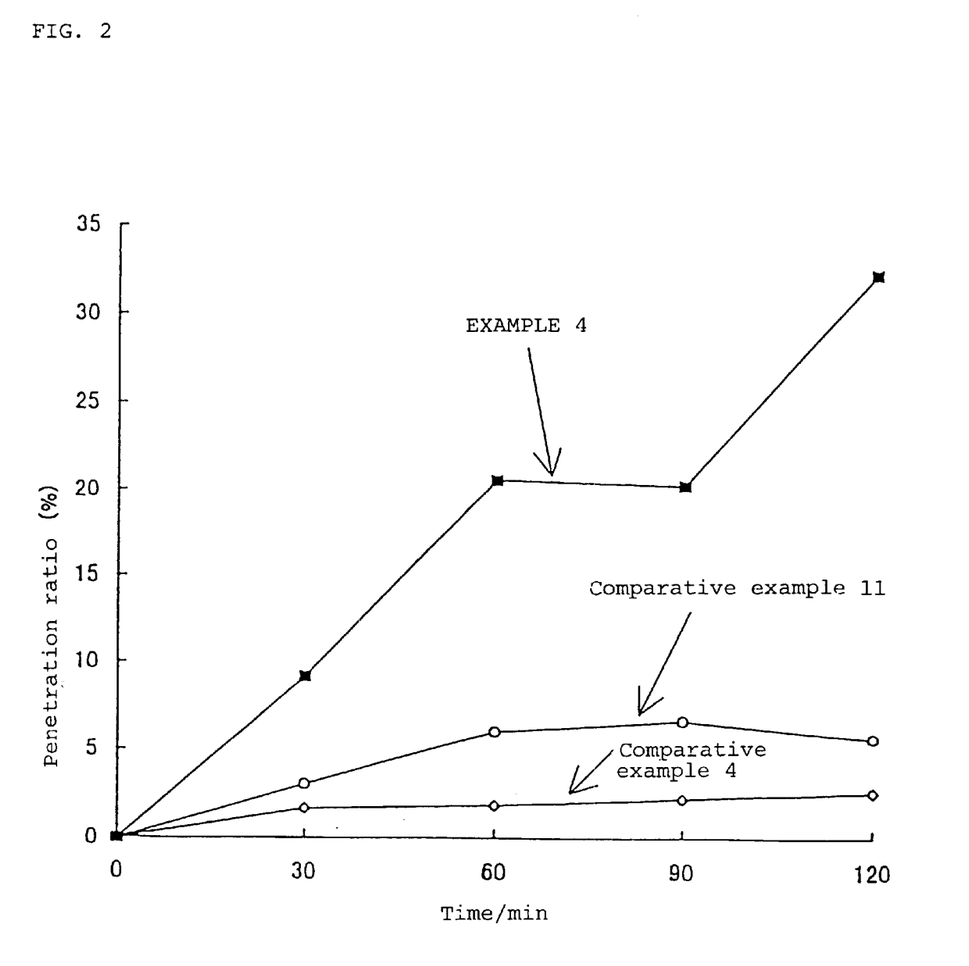
FIG. 2 is a graph showing the relationship between the period of time after application of samples of a skin-whitening cosmetic material to the skin, and the degree of penetration of the unsaturated fatty acids in the samples into the skin.

The data obtained are shown in Tables 1 and 2 and FIGS. 1 and 2.

phospholipid, an antioxidant, a protein or its hydrolyzate, and a muco-polysaccharide, were all found to have a sig-

TABLE 1

| Ingredients | Example | | | | | | | | |
|---|---|---|---|---|---|---|---|---|---|
| | 1 | 2 | 3 | 4 | 5 | 6 | 7 | 8 | 9 |
| Linoleic acid or Linolic acid | 0.50 | | | 0.10 | | | 0.05 | | |
| α-Linolenic acid | | 0.50 | | | | | | 0.05 | |
| Eicosapentaenoic acid | | | | | 0.10 | | | | |
| Ethyl α-linolenate | | | | | | 0.10 | | | 0.05 |
| Linoleic acid monoglyceride | | | 0.50 | | | | | | |
| Lecithin | 0.40 | 0.20 | 0.80 | | 0.20 | | 0.30 | | 0.20 |
| Hydrogenated lecithin | | 0.20 | | 0.40 | | 0.80 | | 0.20 | |
| Vitamin E | 0.05 | 0.01 | 0.10 | 0.05 | 0.01 | 0.10 | 0.05 | 0.01 | 0.10 |
| Collagen | 0.02 | 0.01 | 0.50 | 0.02 | 0.01 | 0.50 | 0.02 | 0.01 | 0.50 |
| Chondroitin sulfate | 0.01 | 0.05 | 0.10 | 0.01 | 0.05 | 0.10 | 0.01 | 0.05 | 0.10 |
| 1,3-Butylene glycol | 5.00 | 5.00 | 5.00 | 5.00 | 5.00 | 5.00 | 5.00 | 5.00 | 5.00 |
| Carboxyvinyl polymer | 0.20 | 0.20 | 0.20 | 0.20 | 0.20 | 0.20 | 0.20 | 0.20 | 0.20 |
| Sodium hydroxide | 0.15 | 0.15 | 0.15 | 0.15 | 0.15 | 0.15 | 0.15 | 0.15 | 0.15 |
| Para-hydroxybenzoate | 0.05 | 0.05 | 0.05 | 0.05 | 0.05 | 0.05 | 0.05 | 0.05 | 0.05 |
| Purified water | ad lib. | ad lib. | ad lib. | ad lib. | ad lib. | ad lib. | ad lib. | ad lib. | ad lib. |
| Effect of anti-pigmentation | ++ | ++ | ++ | ++ | ++ | ++ | ++ | ++ | ++ |

% by weight

TABLE 2

| Ingredients | Comparative example | | | | | | | | |
|---|---|---|---|---|---|---|---|---|---|
| | 1 | 2 | 3 | 4 | 5 | 6 | 7 | 8 | 9 |
| Linoleic acid or Linolic acid | 5.00 | | | 1.00 | | | | | |
| α-Linolenic acid | | | | | | | | 0.50 | |
| Eicosapentaenoic acid | | | 1.50 | | | | | | 0.90 |
| Ethyl α-linolenate | | 3.00 | | | | | | | |
| Linoleic acid monoglyceride | | | | | 0.10 | | | | |
| Linoleic acid triglyceride | | | | | | | | | |
| Lecithin | | | | | | 0.80 | | | |
| Hydrogenated lecithin | | | | | | | | | 0.20 |
| Vitamin E | | | | | | | 0.10 | 0.01 | |
| Collagen | | | | | | | | 0.05 | 0.01 |
| Chondroitin sulfate | | | | | | | | 0.01 | 0.05 |
| 1,3-Butylene glycol | 5.00 | 5.00 | 5.00 | 5.00 | 5.00 | 5.00 | 5.00 | 5.00 | 5.00 |
| Carboxyvinyl polymer | 0.20 | 0.20 | 0.20 | 0.20 | 0.20 | 0.20 | 0.20 | 0.20 | 0.20 |
| Sodium hydroxide | 0.15 | 0.15 | 0.15 | 0.15 | 0.15 | 0.15 | 0.15 | 0.15 | 0.15 |
| Para-hydroxybenzoate | 0.05 | 0.05 | 0.05 | 0.05 | 0.05 | 0.05 | 0.05 | 0.05 | 0.05 |
| Purified water | ad lib. | ad lib. | ad lib. | ad lib. | ad lib. | ad lib. | ad lib. | ad lib. | ad lib. |
| Effect of anti-pigmentation | ++ | ++ | ++ | + | − | − | − | + | ± |

| Ingredients | Comparative example | | | | | | | |
|---|---|---|---|---|---|---|---|---|
| | 10 | 11 | 12 | 13 | 14 | 15 | 16 | 17 |
| Linoleic acid or Linolic acid | | 0.10 | | | | 0.05 | | |
| α-Linolenic acid | | | 0.10 | | | | | |
| Eicosapentaenoic acid | | | | | | | 0.05 | |
| Ethyl α-linolenate | | | | | | | | 0.05 |
| Linoleic acid monoglyceride | 0.50 | | | 0.10 | | | | |
| Linoleic acid triglyceride | | | | | 0.10 | | | |
| Lecithin | 0.40 | | | 0.20 | | | | 0.80 |
| Hydrogenated lecithin | | | 0.40 | | 0.40 | | 0.20 | |
| Vitamin E | 0.05 | 0.10 | | 0.05 | 0.05 | 0.10 | 0.05 | |
| Collagen | | 0.50 | 0.01 | 0.05 | 0.05 | | | 0.10 |
| Chondroitin sulfate | | 0.01 | 0.10 | | 0.05 | 0.10 | 0.05 | 0.05 |
| 1,3-Butylene glycol | 5.00 | 5.00 | 5.00 | 5.00 | 5.00 | 5.00 | 5.00 | 5.00 |
| Carboxyvinyl polymer | 0.20 | 0.20 | 0.20 | 0.20 | 0.20 | 0.20 | 0.20 | 0.20 |
| Sodium hydroxide | 0.15 | 0.15 | 0.15 | 0.15 | 0.15 | 0.15 | 0.15 | 0.15 |
| Para-hydroxybenzoate | 0.05 | 0.05 | 0.05 | 0.05 | 0.05 | 0.05 | 0.05 | 0.05 |
| Purified water | ad lib. | ad lib | ad lib. | ad lib. | ad lib. | ad lib. | ad lib. | ad lib. |
| Effect of anti-pigmentation | + | ± | ± | ± | ± | − | − | − |

% by weight

As is known from Tables 1 and 2 and FIG. 1, the samples of the Examples, which contained, as the essential ingredients, an unsaturated fatty acid or its derivative, a nificant effect in reducing or whitening pigmentation, and these had no trouble of skin irritations.

As opposed to those, the samples of the Comparative Examples had no effect in reducing or whitening pigmentation unless the concentration of the unsaturated fatty acid or its derivative therein was larger than 1% by weight. In addition, the samples of the Comparative Examples not containing any one of the indispensable ingredients of the invention were found to have a poor anti-pigmentation effect.

From FIG. 2, it is known that the skin penetrability of the unsaturated fatty acid in the sample of Example 4, which comprises the liposomal composite, is higher by 5 times or more than that in the samples of Comparative Examples 4 and 11. This will indicate the high effect in reducing or whitening pigmentation in the sample of Example 4.

Example 10
Lotion:

| Ingredients | Amount (%) |
| --- | --- |
| γ-Linolenic acid | 0.1 |
| Glycerin | 5.0 |
| Soybean lecithin | 0.35 |
| Vitamin E | 0.01 |
| Hydrolyzed elastin liquid | 1.0 |
| Sodium hyaluronate | 0.05 |
| Para-hydroxybenzoate | 0.05 |
| Ethanol | 8.0 |
| Citric acid | 0.05 |
| Sodium citrate | 0.07 |
| Fragrance | 0.05 |
| Purified water | balance |
| Total | 100.0 |

Formulation of lotion:
Hydrolyzed elastin liquid and sodium hyaluronate were dissolved in purified water. Apart from this, linoleic acid, soybean lecithin and vitamin E were mixed, and the resulting mixture was added to the aqueous solution prepared above. To the mixture, added were glycerin, citric acid, sodium citrate, ethanol, methyl para-hydroxybenzoate and fragrance, and well stirred to obtain a lotion.

Example 11
Cream:

| Ingredients | Amount (%) |
| --- | --- |
| (A) | |
| Corn lecithin | 0.40 |
| Eicosapentaenoic acid | 0.20 |
| Erythorbic acid | 0.02 |
| Purified water | 10.00 |
| (B) | |
| Sodium chondroitin sulfate | 0.005 |
| Hydrolyzed sodium casein | 0.02 |
| Purified water | 5.00 |
| (C) | |
| Glycerin | 5.00 |
| dl-Pyrrolidone-carboxylic acid | 0.10 |
| Para-hydroxybenzoate | 0.05 |
| Potassium hydroxide | ad lib. (for pH control) |
| Purified water | balance |
| Decaglyceryl monostearate | 1.00 |
| (D) | |
| Stearic acid | 1.00 |
| Cetanol | 2.00 |
| Glyceryl monostearate | 2.00 |
| Squalane | 3.00 |
| Total | 100.0 |

Formulation of cream:
A mixture of the phase (A) was mixed with a uniform solution of the phase (B). Then, the phases (C) and (D) were separately dissolved under heat, and the phase (C) was added to the phase (D), mixed and emulsified using an emulsifying machine. Next, the mixed phase (A) was mixed, stirred and cooled to obtain a cream (pH 7.0).

Example 12
Essence:

| Ingredients | Amount (%) |
| --- | --- |
| (A) | |
| Soybean lecithin | 0.40 |
| Linoleic acid | 0.10 |
| Vitamin E | 0.04 |
| Propylene glycol | 2.00 |
| (B) | |
| Sodium chondroitin sulfate | 0.01 |
| Para-hydroxybenzoate | 0.05 |
| Atelocollagen | 0.05 |
| Propylene glycol | 1.00 |
| Purified water | 10.00 |
| (C) | |
| Purified water | balance |
| Propylene glycol | 5.00 |
| Carboxyvinyl polymer | 0.20 |
| Water-soluble placenta extract | 0.10 |
| Potassium glycyrrhizate | 0.10 |
| Sodium hydroxide | ad lib. (for pH control) |
| Total | 100.00 |

Formulation of essence:
A mixture of the phase (A) was mixed with a uniform solution of the phase (B), using a high-pressure homogenizer, to prepare a liposomal composite, which was then mixed with the phase (C) by stirring them to obtain an essence (pH 6.6).

Example 13
Pack:

| Ingredients | Amount (%) |
| --- | --- |
| (A) | |
| 1,3-Butylene glycol | 7.00 |
| Titanium oxide | 5.00 |
| Talc | 5.00 |

-continued

| Ingredients | Amount (%) |
|---|---|
| Dermatan sulfate | 0.015 |
| Casein | 0.04 |
| Purified water | ad lib. |
| Para-hydroxybenzoate | 0.10 |
| Sodium citrate | 0.20 |
| Polyethylene glycol | 1.00 |
| Hydroxyethyl cellulose | 13.00 |
| (B) | |
| Phosphatidyl choline | 0.60 |
| α-Linolenic acid | 0.70 |
| Hamamelis extract | 0.005 |
| Purified water | 10.00 |
| Total | 100.00 |

Formulation of pack:

The ingredients of the phase (A) were mixed and heated to give a uniform mixture. While cooling the mixture, a mixture of the phase (B) was added thereto with stirring them to give a pack.

Example 14

Cream mask:

| Ingredients | Amount (%) |
|---|---|
| (A) | |
| Para-hydroxybenzoate | 0.20 |
| Glycerin | 8.00 |
| Purified water | balance |
| Triethanolamine | ad lib. (for pH control) |
| POE (20)-sorbitan fatty acid ester | 2.00 |
| (B) | |
| Glycerin monostearate | 3.00 |
| Self-emulsifying glycerin monostearate | 4.00 |
| Stearic acid | 5.00 |
| Liquid paraffin | 7.00 |
| Glyceryl trioctanoate | 4.00 |
| Fragrance | 0.10 |
| (C) | |
| Egg yolk lecithin | 0.60 |
| Arachidonic acid | 0.10 |
| Vitamin E | 0.005 |
| Purified water | 10.00 |
| (D) | |
| Hyaluronic acid | 0.005 |
| Hydrolyzed collagen | 0.02 |
| Purified water | 5.00 |
| Total | 100.00 |

Formulation of cream mask:

The phases (A) and (B) were separately dissolved under heat, and then the phase (A) was added to the phase (B) and mixed by stirring them to give a uniform mixture. On the other hand, a mixture of the phase (C) was mixed with the phase (D), and the resulting mixture was added to and mixed with the phase (B) by stirring them while the phase (B) was cooled. Thus was obtained a cream mask (pH 6.8).

Example 15

Milky lotion:

| Ingredients | Amount (%) |
|---|---|
| (A) | |
| 1,3-Butylene glycol | 5.00 |
| Purified water | balance |
| Para-hydroxybenzoate | 0.30 |
| Decaglyceryl stearate | 2.00 |
| Carboxyvinyl polymer | 0.10 |
| Potassium hydroxide | ad lib. (for pH control) |
| Citric acid | 0.50 |
| (B) | |
| Liquid paraffin | 5.00 |
| Stearic acid | 1.00 |
| Glycerin monostearate | 2.00 |
| Self-emulsifying glycerin monostearate | 1.00 |
| Squalane | 3.00 |
| (C) | |
| Phosphatidyl ethanolamine | 0.06 |
| Phosphatidyl serine | 0.081 |
| Sphingomyelin | 0.108 |
| Ethyl linoleate | 0.20 |
| EDTA | 0.05 |
| Purified water | 10.00 |
| (D) | |
| Sodium chondroitin sulfate | 0.05 |
| Keratin | 0.02 |
| Purified water | 5.00 |
| Total | 100.00 |

Formulation of milky lotion:

The phases (A) and (B) were separately stirred under heat to give mixtures, and the mixture of the phase (A) was added to that of the phase (B) and further mixed by stirring them. On the other hand, the ingredients of the phase (C) were processed in a French press to form liposomes, which were then filtered to dress them. Then, the liposomes were added to the phase (D) to prepare a liposomal composite. This liposomal composite was added to the phase (B) while the phase (B) was cooled. Thus was prepared a milky lotion (pH 6.9).

Example 16

Face wash:

| Ingredients | Amount (%) |
|---|---|
| (A) | |
| Lauric acid | 6.00 |
| Myristic acid | 10.00 |
| Stearic acid | 20.00 |
| Thick glycerin | 10.00 |
| Polyethylene glycol 400 | 10.00 |
| Polyethylene glycol 6000 | 10.00 |
| Polyethylene glycol distearate (150 EO) | 5.00 |
| Purified water | balance |
| Potassium hydroxide | ad lib. (for pH control) |
| Para-hydroxybenzoate | 0.20 |
| Sodium edetate | 0.10 |
| (B) | |
| Lecithin | 0.40 |
| Vitamin E | 0.10 |

-continued

| Ingredients | Amount (%) |
|---|---|
| Ethyl α-linolenate | 0.20 |
| Purified water | 10.00 |
| (C) | |
| Sodium chondroitin sulfate | 0.01 |
| Hydrolyzed collagen | 0.03 |
| Purified water | 5.00 |
| Total | 100.00 |

Formulation of face wash:

The ingredients of the phase (A) were mixed and dissolved under heat. The phases (B) and (C) were separately mixed to give uniform mixtures, and the phase (B) was added to the phase (C). While the phase (A) was cooled, the phase (C) was mixed and stirred with the phase (A). Thus was prepared a face wash (pH 9.6).

Example 17

Cream mask:

| Ingredients | Amount (%) |
|---|---|
| (A) | |
| Para-hydroxybenzoate | 0.20 |
| Glycerin | 8.00 |
| Purified water | balance |
| Triethanolamine | ad lib. (for pH control) |
| POE (20)-sorbitan fatty acid ester | 2.00 |
| (B) | |
| Glycerin monostearate | 3.00 |
| Self-emulsifying glycerin monostearate | 4.00 |
| Stearic acid | 5.00 |
| Liquid paraffin | 7.00 |
| Glycerin trioctanoate | 4.00 |
| Fragrance | 0.10 |
| (C) | |
| Egg yolk lecithin | 0.60 |
| Linoleic acid monoglyceride | 0.10 |
| Vitamin E | 0.005 |
| Sodium hydroxide | ad lib. (for pH control) |
| 1,3-Butylene glycol | 1.00 |
| Purified water | 10.00 |
| (D) | |
| Hyaluronic acid | 0.005 |
| Hydrolyzed collagen | 0.02 |
| Purified water | 5.00 |
| Total | 100.00 |

Formulation of cream mask:

The phases (A) and (B) were separately dissolved under heat to give uniform mixtures. Then, the phase (B) was added to the phase (A) and mixed by stirring them to give a uniform mixture. The ingredients, egg yolk lecithin, linoleic acid monoglyceride and vitamin E were homogenized, and then hydrated with an aqueous solution (pH 6) containing sodium hydroxide and 1,3-butylene glycol to form liposomes (of the phase (C)). The resulting phase (C) was mixed with the phase (D), and added to and mixed with the phase (B) by stirring them while the phase (B) was cooled. Thus was prepared a cream mask (pH 6.8).

Example 18

Essence:

| Ingredients | Amount (%) |
|---|---|
| (A) | |
| Egg yolk lecithin | 0.80 |
| Docosahexaenoic acid | 0.40 |
| Vitamin C | 0.04 |
| Purified water | 10.00 |
| (B) | |
| Chondroitin sulfate | 0.01 |
| Para-hydroxybenzoate | 0.05 |
| Hydrolyzed ethyl collagen | 0.05 |
| Purified water | balance |
| Propylene glycol | 5.00 |
| Carboxyvinyl polymer | 0.20 |
| Potassium hydroxide | ad lib. (for pH control) |
| Total | 100.00 |

Formulation of essence:

The ingredients, egg yolk lecithin, docosahexaenoic acid and vitamin C were mixed in water and ultrasonicated to form liposomes (of the phase (A)). This phase (A) was added to and mixed with a uniform mixture of the phase (B) by stirring them to obtain an essence (pH 6.6).

All the samples of Examples 10 to 18 were found to have an excellent effect in reducing or whitening pigmentation, like the samples of Examples 1 to 9.

INDUSTRIAL APPLICABILITY

The skin-whitening cosmetic material of the invention contains a reduced amount of unsaturated fatty acids, and irritates little the skin to which it has been applied. In addition, the material is highly safe and has an excellent effect in reducing or whitening pigmentation.

What is claimed is:

1. A skin-whitening cosmetic material comprising;
    (A) at least one member selected from the group of compound consisting of unsaturated fatty acids having from 18 to 22 carbon atoms and having from 2 to 6 double bonds in the molecular structure, and their derivatives, wherein the amount of said unsaturated fatty acids and their derivatives is from 0.01 to 0.7% by weight of the total amount of the material,
    (B) a phospholipid,
    (C) an antioxidant in an amount of from 0.0005 to 0.5% by weight,
    (D) at least one member selected from the group of compounds consisting of proteins and their hydrolyzates, and
    (E) chondroitin sulfate.

2. A skin-whitening cosmetic material comprising a liposomal composite that contains the following:
    (A) at least one member selected from the group of compounds consisting of unsaturated fatty acids having from 18 to 22 carbon atoms and having from 2 to 6 double bonds in the molecular structure, and their derivatives, wherein the amount of said unsaturated fatty acids and their derivatives is from 0.01 to 0.7% by weight of the total amount of the material,
    (B) a phospholipid,
    (C) an antioxidant in an amount of from 0.0005 to 0.5% by weight, (D) at least one member selected from the group of compounds consisting of proteins and their hydrolyzates, and (E) chondroitin sulfate.

3. The skin-whitening cosmetic material as claimed in claim 1, wherein the phospholipid is at least one member selected from the group of compounds consisting of soybean lecithin, egg yolk lecithin, hydrogenated soybean lecithin and hydrogenated egg yolk lecithin.

4. The skin-whitening cosmetic material as claimed in claim 1, wherein the protein or its hydrolyzate is at least one member selected from the group of compounds consisting of collagen, elastin and their hydrolyzates, and salts and esters of their hydrolyzates.

5. The skin-whitening cosmetic material as claimed in claim 1, wherein the chondroitin sulfate is present in an amount of from 0.0005 to 0.5% by weight.

6. The skin-whitening cosmetic material as claimed in claim 2, wherein the phospholipid is at least one member selected from the group of compounds consisting of soybean lecithin, egg yolk lecithin, hydrogenated soybean lecithin and hydrogenated egg yolk lecithin.

7. The skin-whitening cosmetic material as claimed in claim 2, wherein the protein or its hydrolyzate is at least one member selected from the group of compounds consisting of collagen, elastin and their hydrolyzates, and salts and esters of their hydrolyzates.

8. The skin-whitening cosmetic material as claimed in claim 2, wherein the chondroitin sulfate is present in an amount of from 0.0005 to 0.5% by weight.

9. The skin-whitening cosmetic material as claimed in claim 2, wherein the liposomal composite is prepared by forming liposomes in water as a result of mixing the following:

(A) at least one member selected from the group of compounds consisting of unsaturated fatty acids having from 18 to 22 carbon atoms and having from 2 to 6 double bonds in the molecular structure, and their derivatives, (B) a phospholipid, and (C) an antioxidant, followed by mixing the resulting liposomes with an aqueous solution containing the following:

(D) at least one member selected from the group of compounds consisting of proteins and their hydrolyzates, and (E) at least one member selected from the group of compounds consisting of muco-polysaccharides and their salts.

10. The skin-whitening cosmetic material as claimed in claim 2, wherein the liposomal composite is prepared by forming liposomes in an aqueous solution containing the following:

(D) at least one member selected from the group of compounds consisting of proteins and their hydrolyzates, and (E) at least one member selected from the group of compounds consisting of muco-polysaccharides and their salts, said liposomes comprising the following:

(A) at least one member selected from the group of compounds consisting of unsaturated fatty acids having from 18 to 22 carbon atoms and having from 2 to 6 double bonds in the molecular structure, and their derivatives, (B) a phospholipid, and (C) an antioxidant.

\* \* \* \* \*